US009283119B2

(12) United States Patent
Maruhata (10) Patent No.: US 9,283,119 B2
(45) Date of Patent: Mar. 15, 2016

(54) PARTICLE SUPPLYING APPARATUS AND SHEET ARTICLE MANUFACTURING APPARATUS

(75) Inventor: Kazuya Maruhata, Mima-gun (JP)

(73) Assignee: LIVEDO CORPORATION, Shikokuchuo-shi (JP)

( * ) Notice: Subject to any disclaimer, the term of this patent is extended or adjusted under 35 U.S.C. 154(b) by 249 days.

(21) Appl. No.: 14/130,447

(22) PCT Filed: Jul. 5, 2012

(86) PCT No.: PCT/JP2012/004388
§ 371 (c)(1),
(2), (4) Date: Dec. 31, 2013

(87) PCT Pub. No.: WO2013/008432
PCT Pub. Date: Jan. 17, 2013

(65) Prior Publication Data
US 2014/0144587 A1 May 29, 2014

(30) Foreign Application Priority Data

Jul. 8, 2011 (JP) ................................ 2011-151579

(51) Int. Cl.
*B28B 19/00* (2006.01)
*B29C 65/52* (2006.01)
(Continued)

(52) U.S. Cl.
CPC ..... *A61F 13/15577* (2013.01); *A61F 13/15658* (2013.01); *A61F 13/15699* (2013.01);
(Continued)

(58) Field of Classification Search
CPC .... B32B 27/00; B32B 27/12; B32B 37/0053; B32B 37/20; B32B 37/22; B32B 37/24; B32B 2555/02; B05C 1/0808; B05C 1/081; B05C 1/04; B05C 1/10; B05C 1/16; B05C 5/0233; B05C 5/0245; B05C 19/00; B05C 19/04; B05C 19/06; A61F 13/15; A61F 13/15577; A61F 13/15658; A61F 13/15699; A61F 13/15764; A61F 13/15804; B29C 39/10; B29C 65/18; B29C 66/80; B29C 66/83411; B29C 66/83413; B05D 1/02; B05D 1/06; B05D 1/28; B05D 7/54; C09J 5/06; B65H 37/02

USPC ................................. 156/390, 553, 555, 582
See application file for complete search history.

(56) References Cited

U.S. PATENT DOCUMENTS 4,851,069 A * 7/1989 Packard .............. A61F 13/1565
156/276
4,994,053 A * 2/1991 Lang ................ A61F 13/15634
428/117

(Continued)

FOREIGN PATENT DOCUMENTS

CN     1089465 A     7/1994
CN     1954108 A     4/2007
(Continued)

OTHER PUBLICATIONS

International Search Report dated Oct. 30, 2012 issued in corresponding application No. PCT/JP2012/004388.
(Continued)

*Primary Examiner* — Sing P Chan
(74) *Attorney, Agent, or Firm* — Westerman, Hattori, Daniels & Adrian, LLP (57) ABSTRACT

An absorbent sheet manufacturing apparatus has a cylinder part having a plurality of concave portions arranged in a circumferential direction, a particle filling part which is located above the cylinder part and which stores particles of high-absorbent resin, to sequentially fill the plurality of concave portions with particles by a particle filling opening in its lower end, and a communication part which is located adjacent to the particle filling opening. A concave portion facing a posterior edge of the particle filling opening is brought into communication with external space through the communication part. Therefore, when particles are filled into the concave portion from the particle filling part, air in the concave portion is forced out by particles entering the concave portion and is easily discharged to the external space through the communication part. As a result, it is possible to increase a density of particles filled in the concave portion.

16 Claims, 5 Drawing Sheets

(51) Int. Cl.
  *B32B 37/24* (2006.01)
  *B32B 38/18* (2006.01)
  *B31F 5/00* (2006.01)
  *A61F 13/15* (2006.01)
  *B05C 1/08* (2006.01)
  *B05C 1/10* (2006.01)
  *B05C 1/16* (2006.01)
  *B05C 19/00* (2006.01)
  *B05C 19/06* (2006.01)

(52) U.S. Cl.
  CPC ..... *A61F13/15764* (2013.01); *A61F 13/15804* (2013.01); *B05C 1/0808* (2013.01); *B05C 1/0813* (2013.01); *B05C 1/10* (2013.01); *B05C 1/16* (2013.01); *B05C 19/00* (2013.01); *B05C 19/06* (2013.01)

(56) References Cited

U.S. PATENT DOCUMENTS

| | | | | |
|---|---|---|---|---|
| 7,744,713 | B2 * | 6/2010 | Blessing | A61F 13/15658 156/196 |
| 8,163,124 | B2 * | 4/2012 | Moriura | A61F 13/15658 156/276 |
| 2006/0278335 | A1 * | 12/2006 | Moriura | A61F 13/15658 156/279 |
| 2007/0227679 | A1 | 10/2007 | Maruhata | |
| 2009/0056867 | A1 * | 3/2009 | Moriura | A61F 13/15658 156/276 |
| 2014/0099429 | A1 * | 4/2014 | Maruhata | A61F 13/1565 427/8 |
| 2014/0116626 | A1 * | 5/2014 | Maruhata | A61F 13/15658 156/547 |
| 2014/0124143 | A1 * | 5/2014 | Maruhata | A61F 13/15658 156/383 |
| 2014/0138031 | A1 * | 5/2014 | Maruhata | A61F 13/15658 156/390 |
| 2014/0144586 | A1 * | 5/2014 | Maruhata | B05C 19/04 156/390 |

FOREIGN PATENT DOCUMENTS

| | | |
|---|---|---|
| EP | 1 621 165 A1 | 2/2006 |
| EP | 1 621 166 A1 | 2/2006 |
| EP | 1621167 A2 | 2/2006 |
| EP | 1 655 007 A1 | 5/2006 |
| EP | 1655077 A2 | 5/2006 |
| EP | 1700586 A2 | 9/2006 |
| EP | 2 412 346 A1 | 2/2012 |
| EP | 2 444 045 A1 | 4/2012 |
| JP | 2005-59579 A | 3/2005 |
| JP | 2009-000386 A | 1/2009 |
| JP | 2010-246989 A | 11/2010 |
| WO | 94/07547 A1 | 4/1994 |
| WO | 2005/067846 A1 | 7/2005 |

OTHER PUBLICATIONS

Written Opinion of the International Searching Authority dated Oct. 30, 2012 issued in corresponding application No. PCT/JP2012/004388.

* cited by examiner

PARTICLE SUPPLYING APPARATUS AND SHEET ARTICLE MANUFACTURING APPARATUS

TECHNICAL FIELD

The present invention relates to a particle supplying apparatus for supplying particles of absorbent material or deodorant material onto a sheet member, and a sheet article manufacturing apparatus comprising the particle supplying apparatus for manufacturing a sheet article for an absorbent article.

BACKGROUND ART

In an absorbent article such as an absorbent pad for light incontinence which is used by being attached on the inside of a disposable diaper, an absorbent sheet is conventionally utilized which is obtained by sandwiching particles of high-absorbent resin between two sheet members formed of nonwoven fabric or the like to fix the particles therebetween.

Japanese Patent Application Laid-Open No. 2005-59579 (Document 1) is related to a manufacturing apparatus for manufacturing a sheet-like absorbent body used for a disposable absorbent article. The apparatus is provided with a temporary receiving roller having an outer side surface on which a plurality of concave grooves intermittently arranged in a circumferential direction are formed, a transfer roller for holding a base sheet under the temporary receiving roller to convey the base sheet, a box located above the temporary receiving roller for supplying high-absorbent resin particles into the above plurality of concave grooves, and an arcuate guide member facing the outer side surface of the temporary receiving roller in a region from the box to the transfer roller to hold the high-absorbent resin particles supplied in the plurality of concave grooves. The high-absorbent resin particles held in the plurality of concave grooves in the temporary receiving roller are moved to a lower position by rotation of the temporary receiving roller, to be supplied onto the base sheet on which hot melt adhesive is applied. Then, by bonding a cover sheet on the base sheet with high-absorbent resin particles placed therebetween, the sheet-like absorbent body is formed.

Incidentally, in the apparatus of Document 1, when high-absorbent resin particles are supplied into the plurality of concave grooves from the box, it isn't easy to increase a fill density of particles in each concave groove due to air existing in the concave groove. Especially, in the case where the temporary receiving roller having the plurality of concave grooves is rotated at a high speed, the time for filling particles into each concave groove becomes short and as a result, it is more difficult to increase the fill density of particles in the concave groove.

SUMMARY OF INVENTION

The present invention is intended for a particle supplying apparatus for supplying particles of absorbent material or deodorant material onto a sheet member. It is an object of the present invention to increase a density of particles filled in each concave portion.

The particle supplying apparatus according to the present invention comprises: a cylinder part which has an generally cylindrical shape rotated around a rotation axis along a horizontal direction, the cylinder part having a plurality of concave portions arranged in a circumferential direction on an outer side surface thereof; a particle filling part which is located above the cylinder part and which stores particles of absorbent material or deodorant material, to sequentially fill the plurality of concave portions with particles by a particle filling opening which faces the outer side surface of the cylinder part; a first cover part which spreads from the particle filling opening along a rotation direction of the cylinder part to cover a portion of the outer side surface of the cylinder part; a second cover part which spreads from the particle filling opening along an opposite direction of the rotation direction to cover another portion of the outer side surface of the cylinder part; a communication part which is located adjacent and posterior to the particle filling opening in the rotation direction, a concave portion out of the plurality of concave portions being in communication with external space through the communication part, the concave portion facing a posterior edge of the particle filling opening; and a sheet conveying part for conveying a sheet member in a direction under an anterior edge of the first cover part in the rotation direction, the direction being same as a moving direction of the outer side surface of the cylinder part.

In the present invention, it is possible to increase a density of particles filled in each concave portion.

According to a preferred embodiment of the present invention, the particle filling opening faces a portion including an uppermost portion of the cylinder part. Therefore, filling of particles into the concave portion due to gravity is promoted and the density of particles filled in the concave portion can be further increased.

According to another preferred embodiment of the present invention, one end portion of the communication part which faces the cylinder part is positioned below the other end portion of the communication part. This can reduce escape of particles from the concave portion to the external space through the communication part.

According to still another preferred embodiment of the present invention, the particle supplying apparatus further comprises a suction part for suctioning gas in the communication part. As a result, the density of particles filled in each concave portion can be increased further.

The present invention is also intended for a sheet article manufacturing apparatus for manufacturing a sheet article for an absorbent article. The sheet article manufacturing apparatus comprises the above particle supplying apparatus; another sheet conveying part for conveying another sheet member; and a sheet bonding part for placing the another sheet member on the sheet member which has been supplied with particles by the particle supplying apparatus, to bond the another sheet member on the sheet member.

These and other objects, features, aspects and advantages of the present invention will become more apparent from the following detailed description of the present invention when taken in conjunction with the accompanying drawings.

DESCRIPTION OF EMBODIMENTS

Figure 1:
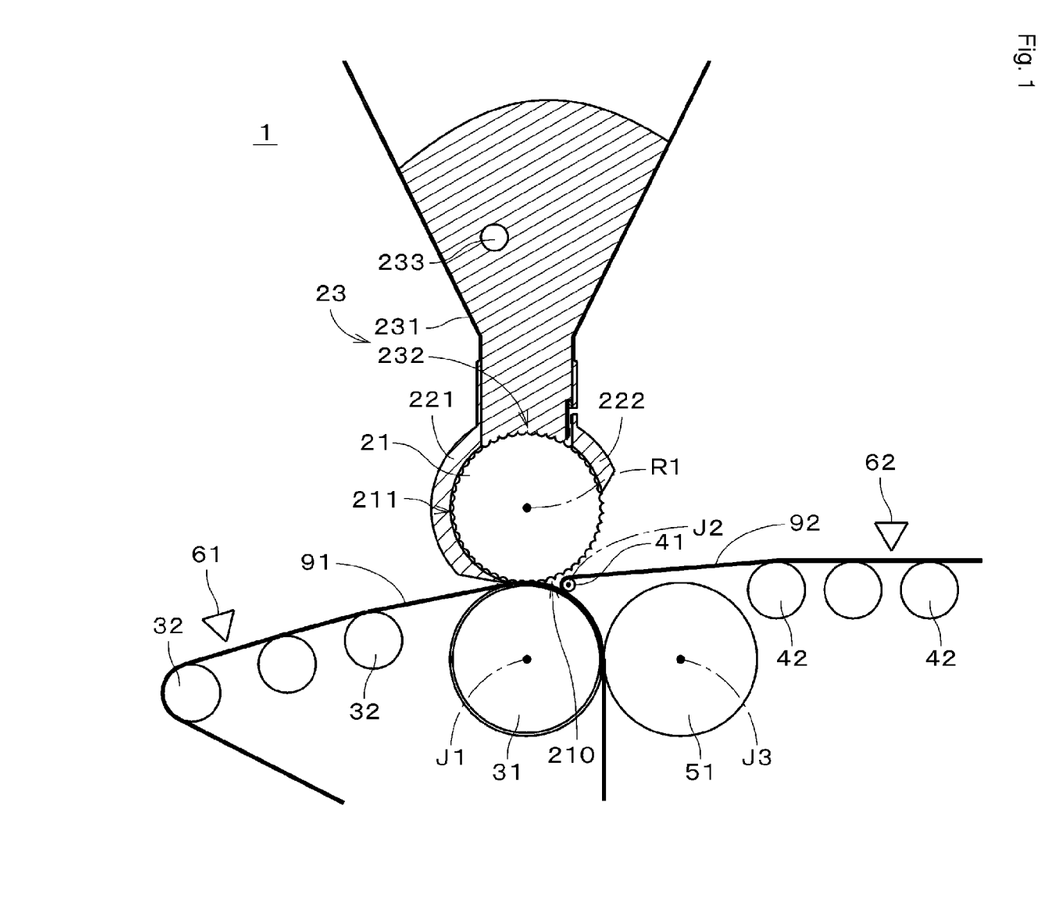
FIG. 1 is a view showing an absorbent sheet manufacturing apparatus in accordance with a preferred embodiment.

FIG. 1 is a view showing an absorbent sheet manufacturing apparatus 1 in accordance with a preferred embodiment of the present invention. The absorbent sheet manufacturing apparatus 1 is one sheet article manufacturing apparatus for manufacturing a sheet article for an absorbent article and manufactures absorbent sheets by sandwiching particles of high-absorbent resin such as SAP (Super Absorbent Polymer) between sheet members formed of nonwoven fabric or the like. The absorbent sheet is a sheet article used for an absorbent article such as a disposable diaper or absorbent pad for light incontinence.

The absorbent sheet manufacturing apparatus 1 has a cylinder part 21 which is a generally cylindrical member around (with its center lying on) a rotation axis R1 along (toward) a horizontal direction, a first sheet conveying roller 31 having a generally columnar shape around a first central axis J1 parallel to a direction along the rotation axis R1 (hereinafter, the direction is referred to as an "axial direction"), a second sheet conveying roller 41 having a generally columnar shape around a second central axis J2 parallel to the axial direction, and a bonding roller 51 having a generally columnar shape around a third central axis J3 parallel to the axial direction. The first central axis J1 is positioned right below the rotation axis R1 in the vertical direction. The absorbent sheet manufacturing apparatus 1 also has a plurality of auxiliary rollers 32, 42 each having a generally columnar shape around a central axis parallel to the axial direction, and a first applying part 61 and second applying part 62 each for applying adhesive (in the present embodiment, hot melt adhesive).

The cylinder part 21, the second sheet conveying roller 41, the bonding roller 51 and the auxiliary rollers 42 are rotated in a counterclockwise direction in FIG. 1, and the first sheet conveying roller 31 and the auxiliary rollers 32 are rotated in a clockwise direction in FIG. 1. The first sheet conveying roller 31 is a sheet conveying part for conveying a first sheet member 91, which is continuous sheet formed of nonwoven fabric or the like, to a vicinity of a lowermost portion of the cylinder part 21. The first applying part 61 is located above the plurality of auxiliary rollers 32, and applies adhesive onto the first sheet member 91.

The second sheet conveying roller 41 is a sheet conveying part for conveying a second sheet member 92, which is continuous sheet formed of nonwoven fabric or the like, to the vicinity of the lowermost portion of the cylinder part 21. The second applying part 62 is located above the plurality of auxiliary rollers 42, and applies adhesive onto the second sheet member 92. The cylinder part 21 supplies particles of high-absorbent resin (hereinafter, simply referred to as "particles") onto the first sheet member 91 in the vicinity of the lowermost portion. The bonding roller 51 is provided beside the first sheet conveying roller 31. The bonding roller 51 is a sheet bonding part for bonding the first sheet member 91 and the second sheet member 92 with each other by overlapping the first sheet member 91 and the second sheet member 92 with each other and sandwiching them between the first sheet conveying roller 31 and the bonding roller 51.

A particle filling part 23 is provided above the cylinder part 21. The particle filling part 23 has a particle tank 231 which is located above the cylinder part 21 and which stores the particles of high-absorbent resin, and a level sensor 233 provided to the particle tank 231. When the level sensor 233 detects that the amount of particles stored in the particle tank 231 becomes equal to or less than a certain level, particles are replenished into the particle tank 231. The particle tank 231 extends almost in parallel with the vertical direction (i.e., direction of gravitational force), and a particle filling opening 232 facing the outer side surface 211 of the cylinder part 21 is provided to a lower end of the particle tank 231. The particle filling opening 232 faces a portion including the uppermost portion of the cylinder part 21.

A first cover part 221 which covers a portion of the outer side surface 211 of the cylinder part 21 and a second cover part 222 which covers another portion of the outer side surface 211 are provided around the cylinder part 21. The first cover part 221 spreads from the particle filling opening 232 to the vicinity of the lowermost portion of the cylinder part 21 along the rotation direction of the cylinder part 21 (i.e., in the counterclockwise direction in FIG. 1), to cover the outer side surface 211 in the left side of the cylinder part 21. The second cover part 222 spreads from the particle filling opening 232 to a vicinity of a right end portion of the cylinder part 21 along an opposite direction of the rotation direction of the cylinder part 21 (i.e., toward the posterior side in the rotation direction (that is, in the clockwise direction in FIG. 1)), to cover the outer side surface 211 in the right side of the cylinder part 21.

In the outer side surface 211 of the cylinder part 21, a region between the lower end of the first cover part 221 and the lower end of the second cover part 222, that is a region which is not covered with the first cover part 221 and the second cover part 222 in the lower side of the cylinder part 21, is an after-mentioned particle supply region 210. The first cover part 221 spreads from the particle supply region 210 in the clockwise direction, and the second cover part 222 spreads from the particle supply region 210 in the counterclockwise direction.

Figure 2:
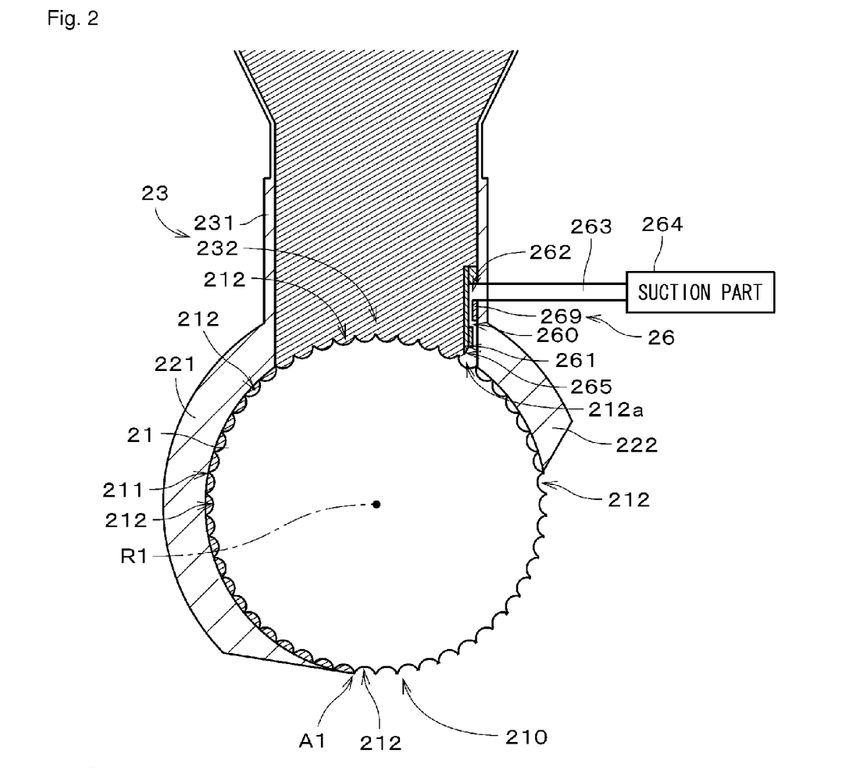
FIG. 2 is a cross-sectional view of a vicinity of a cylinder part.
Figure 3:
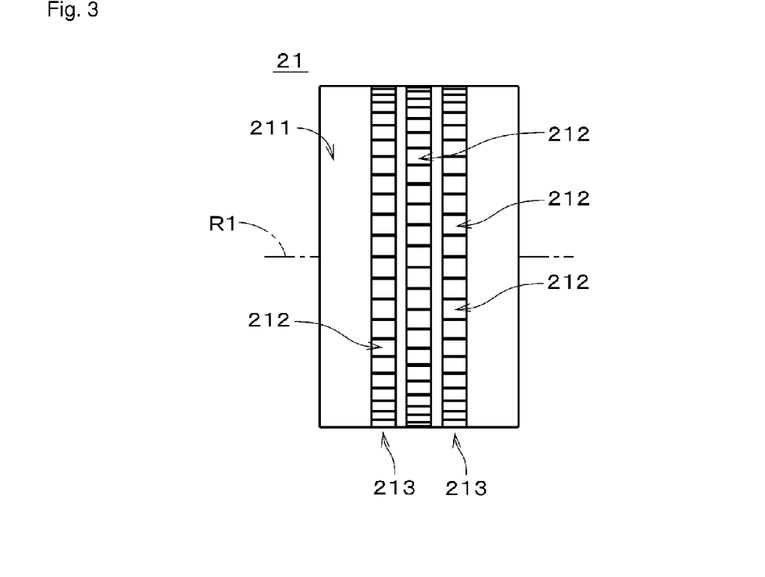
FIG. 3 is a front view of the cylinder part.

FIG. 2 is an enlarged cross-sectional view showing the vicinity of the cylinder part 21, and shows a cross section which is orthogonal to the rotation axis R1. FIG. 3 is a view showing the outer side surface 211 of the cylinder part 21, and in FIG. 3, an appearance of the outer side surface 211 of the cylinder part 21 which is observed along a direction orthogonal to the rotation axis R1 is shown. In FIG. 2, regions of the particles are densely hatched. In FIG. 3, the first cover part 221 and the second cover part 222 are omitted.

As shown in FIGS. 2 and 3, with respect to each of a plurality of positions in the axial direction, a plurality of concave portions 212 are arranged densely (closely with each other) on (in) the outer side surface 211 of the cylinder part 21 in a circumferential direction around the rotation axis R1. When the plurality of concave portions 212 which are arranged in the circumferential direction at the same position in the axial direction are referred to as a concave portion row 213, three concave portion rows 213 are provided in the cylinder part 21 as shown in FIG. 3. In the present embodiment, the shape of each concave portion 212 observed along a direction orthogonal to the rotation axis R1 is generally rectangular. In a cross section orthogonal to the rotation axis R1, the shape of a bottom surface of each concave portion 212 is generally arc-like as shown in FIG. 2. The concave portions 212 may have a various shape, for example, the shape of each concave portion 212 in the cross section orthogonal to the rotation axis R1 may be generally rectangular. On the cylinder outer side surface 211, one, two, four or more supply concave portion rows 213 may be provided.

The outer side surface 211 of the cylinder part 21 is very close to an inner side surface of the first cover part 221 and an inner side surface of the second cover part 222 in regions where the concave portions 212 don't exist, and the outer side surface 211 is substantively in contact with these inner side surfaces.

In the absorbent sheet manufacturing apparatus 1, the cylinder part 21 is rotated around the rotation axis R1 at a high speed, and particles are sequentially filled from the particle tank 231 of the particle filling part 23 into the plurality of concave portions 212 passing the particle filling opening 232 due to gravity. A communication part 26 located adjacent to the particle filling opening 232 is provided to the right of the particle filling opening 232 in FIG. 2 (i.e., posterior to the particle filling opening 232 in the rotation direction of the cylinder part 21). A concave portion 212a out of the plurality of concave portions 212 (the concave portion is denoted by a reference sign 212a in order to be distinguished from the other concave portions 212), which faces a posterior edge of the particle filling opening 232 (i.e., a posterior end in the rotation direction of the cylinder part 21) in the cylinder part 21, is brought into communication with external space by the communication part 26. In FIG. 2, the cross section of the communication part 26 at the position II-II in after-mentioned FIG. 4 is drawn in order to facilitate understanding of the drawing.

Figure 4:
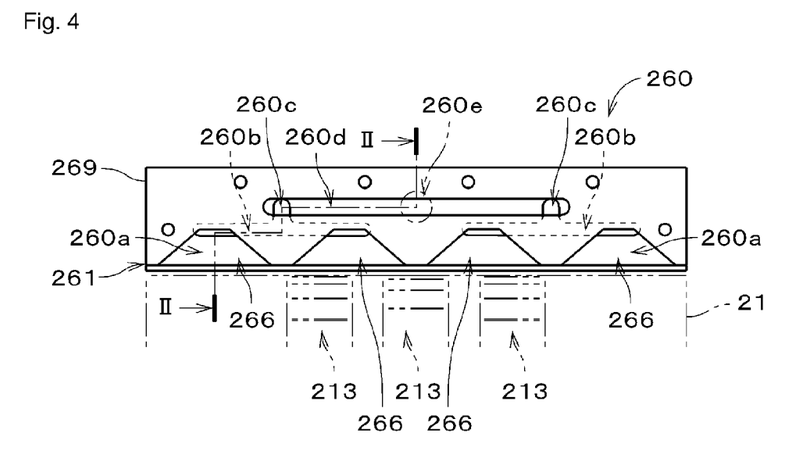
FIG. 4 is a view showing a communication part-forming member.

FIG. 4 is a view showing a plate-like communication part-forming member 269 which forms the communication part 26, and shows an appearance of the communication part-forming member 269 which is observed from the right side of the particle tank 231 in FIG. 2. In FIG. 4, the upper portion of the cylinder part 21 is also drawn together with the communication part-forming member 269. A plurality of grooves are formed on both main surface of the communication part-forming member 269. As shown in FIG. 2, the communication part-forming member 269 is fixed on a right inner side surface of the particle tank 231, and the left main surface of the communication part-forming member 269 is covered with a plate member. Therefore, the above grooves become a communication path 260 of the communication part 26.

In the communication part 26, a first end portion 261 is one end portion which faces the cylinder part 21, and the first end portion 261 is positioned below a second end portion 262 which is the other end portion of the communication part 26 located on the external space side of the communication part 26. In the present embodiment, the first end portion 261 is almost right below the second end portion 262 in the vertical direction. A suction part 264 for suctioning gas in the communication part 26 is connected to the second end portion 262 through a pipe 263. The suction part 264 has a regulator for adjusting a suction pressure and performs suction weakly.

As shown in FIG. 4, the first end portion 261 of the communication part 26 is provided with four communication openings 266. The plurality of communication openings 266 are arranged across almost the entire extent where the three concave portion rows 213 are arranged in the axial direction (i.e., the left-right direction in FIG. 4) of the cylinder part 21.

The communication path 260 in the communication part 26 has four first flow paths 260a extending upwardly from the communication openings 266 respectively, two second flow paths 260b each extending in the axial direction to connect upper end portions of two first flow paths 260a to each other, two third flow paths 260c extending upwardly from middle portions of the two second flow paths 260b respectively, one fourth flow path 260d connecting upper end portions of the two third flow paths 260c to each other, and one fifth flow path 260e connecting a middle portion of the fourth flow path 260d to the external space. The first flow paths 260a and the fourth flow path 260d are formed on one main surface (a front main surface in FIG. 4) of the communication part-forming member 269, and the second flow paths 260b and the third flow paths 260c are formed on the other main surface (i.e., behind the first flow paths 260a and the fourth flow path 260d in FIG. 4) of the communication part-forming member 269. A path width of each first flow path 260a in a direction parallel with the axial direction gradually decreases with distance upward from the communication opening 266.

The communication path 260 extends upward from each communication opening 266, and bends at the upper end portion of the first flow path 260a to extend backward in FIG. 4 (i.e., in a thickness direction of the communication part-forming member 269). And, the communication path 260 bends to extend in parallel with the axial direction, and bends at the middle portion of the second flow path 260b to extend upward. Furthermore, the communication path 260 bends at the upper end portion of the third flow path 260c to extend frontward in FIG. 4, and further bends to extend in parallel with the axial direction. Then, the communication path 260 bends at the middle portion of the fourth flow path 260d to extend frontward in FIG. 4 (i.e., becomes the fifth flow path 260e), and therefore communicates with the external space. As above, the communication path 260 has many bending portions (bends at many points).

Figure 5:
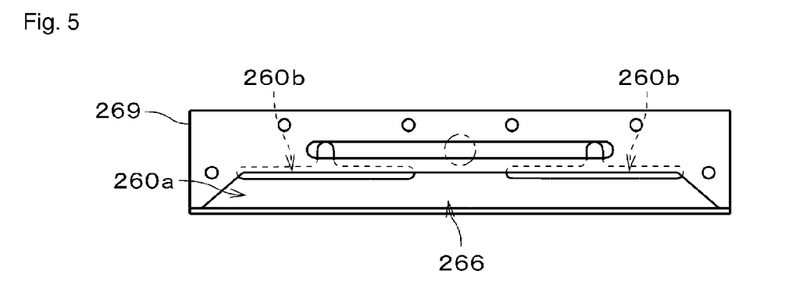
FIG. 5 is a view showing the communication part-forming member.

In the communication part-forming member 269, as shown in FIG. 5, only one communication opening 266 and one first flow path 260a may be provided at a position corresponding to the four communication openings 266 and the four first flow paths 260a in FIG. 4. In this case, the two second flow paths 260b are connected to an upper end portion of the first flow path 260a.

As shown in FIG. 2, in the first end portion 261, an end portion-side surface 265 facing the communication path 260 is an inclined surface extending toward the lower left in FIG. 2. In the absorbent sheet manufacturing apparatus 1, when the rotation of the cylinder part 21 is stopped or the like, a small amount of particles sometimes enters the communication path 260. In this case, when the rotation of the cylinder part 21 is started again, the first end portion 261 of the communication part 26 is pressed by the particles. In the communication part 26, as mentioned previously, the end portion-side surface 265 is the inclined surface where a portion closer to the cylinder part 21 is positioned anterior in the rotation direction of the cylinder part 21. Therefore, when the rotation of the cylinder part 21 is started again, particles in the communication path 260 easily move downward along the end portion-side surface 265 and fall out from the communication path 260. As a result, the end portion-side surface 265 is prevented from being compressed hard by the particles in the communication path 260.

In the absorbent sheet manufacturing apparatus 1, until each concave portion 212 filled with particles reaches the particle supply region 210 provided in the lower portion of the cylinder part 21, the outer end of the concave portion 212 is closed (blocked) with the first cover part 221 (that is, the concave portion 212 is covered on the outer side surface 211). When each concave portion 212 pass the particle supply region 210 beyond an edge of the first cover part 221 in the vicinity of the lowermost portion of the cylinder part 21, that is, beyond an anterior edge of the first cover part 221 in the rotation direction of the cylinder part 21, particles filled in the concave portion 212 are ejected out of the cylinder part 21.

Specifically, ejection of particles is started at the moment (an anterior portion of) the concave portion 212 has passed over the above edge of the first cover part 221. In the following description, a position of the above edge is referred to as an "ejection start position A1". The ejection start position A1 lies posterior to (upstream of) the lowermost portion of the cylinder part 21 in the rotation direction of the cylinder part 21 and is positioned in the vicinity of the lowermost portion of the cylinder part 21. As mentioned previously, the cylinder part 21 is rotated at a high speed, and particles are sequentially ejected from the plurality of concave portions 212 almost along a tangent line of the outer side surface 211 at the ejection start position A1. Each concave portion 212 which has ejected particles passes through the particle supply region 210, and is moved to the upper portion of the cylinder part 21 with its outer end closed by the second cover part 222, to go to the particle filling opening 232 of the particle filling part 23.

Figure 6:
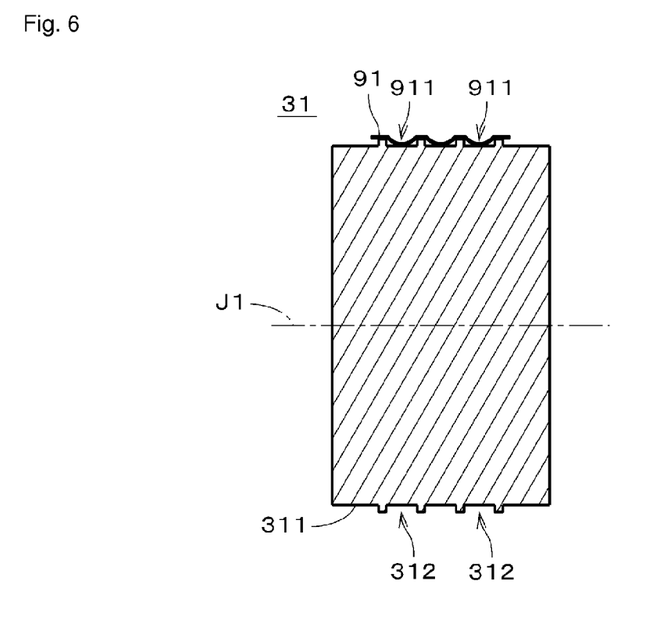
FIG. 6 is a cross-sectional view of a first sheet conveying roller.

FIG. 6 is a cross-sectional view of the first sheet conveying roller 31 and shows a cross section of the first sheet conveying roller 31 taken along a plane including the rotation axis R1 of the cylinder part 21 in FIG. 1 and the first central axis J1 of the first sheet conveying roller 31. The first sheet conveying roller 31 has an outer side surface 311 which is a generally cylindrical surface around the first central axis J1, and an annular groove 312 along a circumferential direction around the first central axis J1 is formed on the outer side surface 311 with respect to each of the plurality of positions in the axial direction. The annular grooves 312 are located at the same positions in the axial direction as the positions of the concave portion rows 213 (see FIG. 3) in the cylinder part 21.

The first sheet member 91 is led to the first sheet conveying roller 31 through the plurality of auxiliary rollers 32 (see FIG. 1). At this time, adhesive is applied by the first applying part 61 onto only a plurality of strip-like regions (or linear regions) on the first sheet member 91 which are overlapped with the plurality of annular grooves 312, respectively. Positions of the plurality of strip-like regions (hereinafter referred to as "adhesive-applied regions") are identical to the positions of the plurality of concave portion rows 213 in the cylinder part 21 and the positions of the plurality of annular grooves 312 with respect to the axial direction. The first sheet member 91 under the ejection start position A1 (see FIG. 2) of the particle supply region 210 is conveyed by the first sheet conveying roller 31 in the same direction as a moving direction of the outer side surface 211 of the cylinder part 21 (i.e., rightward in FIG. 1). From the cylinder part 21, particles are ejected toward the plurality of adhesive-applied regions on the first sheet member 91 to be held on the first sheet member 91.

In the first sheet conveying roller 31, a diameter of the outer side surface 311 is comparatively-large, and also the first sheet member 91 is stretched along the outer side surface 311 at a certain tension. Therefore, a portion 911 of the first sheet member 91 corresponding to each annular groove 312 becomes a shape depressed toward the bottom of the annular groove 312. In other words, groove portions 911 corresponding to the annular grooves 312 are formed on the first sheet member 91. As mentioned previously, the positions of the annular grooves 312 in the first sheet conveying roller 31 are same as the positions of the concave portion rows 213 with respect to the axial direction. Thus, most particles ejected from each concave portion 212 go toward the groove portion 911 to be collected in the groove portion 911. At this time, even if particles bounce from the first sheet member 91 in the groove portions 911, scattering of particles to the outside of the groove portions 911 is suppressed (reduced) by side walls of the groove portions 911. In addition, since the above adhesive-applied regions on the first sheet member 91 are positioned at the groove portions 911, particles are easily caught in the groove portions 911.

Figure 7:
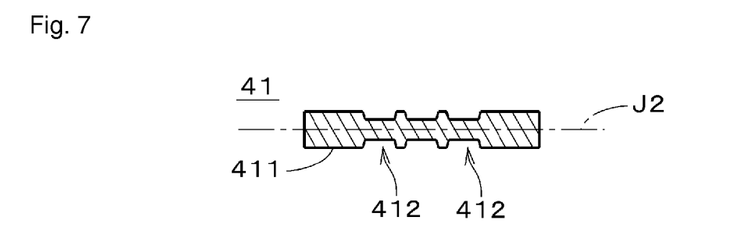
FIG. 7 is a cross-sectional view of a second sheet conveying roller.

FIG. 7 is a cross-sectional view of the second sheet conveying roller 41 and shows a cross section of the second sheet conveying roller 41 taken along a plane including the second central axis J2 of the second sheet conveying roller 41 in FIG. 1. The second sheet conveying roller 41 has an outer side surface 411 which is a generally cylindrical surface around the second central axis J2, and an annular groove 412 along a circumferential direction around the second central axis J2 is formed on the outer side surface 411 with respect to each of the plurality of positions in the axial direction. The plurality of annular grooves 412 are located at the same positions in the axial direction as the positions of the plurality of concave portion rows 213 in the cylinder part 21 and the positions of the plurality of annular grooves 312 in the first sheet conveying roller 31.

The second sheet member 92 is led to the second sheet conveying roller 41 through the plurality of auxiliary rollers 42 (see FIG. 1). At this time, adhesive is applied by the second applying part 62 onto only a plurality of strip-like (or linear) adhesive-applied regions on the second sheet member 92 which are overlapped with the plurality of annular grooves 412. Positions of the plurality of adhesive-applied regions are identical to the positions of the plurality of concave portion rows 213 in the cylinder part 21 and the positions of the plurality of annular grooves 312 in the first sheet conveying roller 31 with respect to the axial direction. Some of particles ejected from each concave portion 212 of the cylinder part 21 bounce from the first sheet member 91 in the groove portion 911 (see FIG. 6) to go toward the second sheet conveying roller 41, and others go from the concave portion 212 of the cylinder part 21 to the second sheet conveying roller 41 directly.

Figure 8:
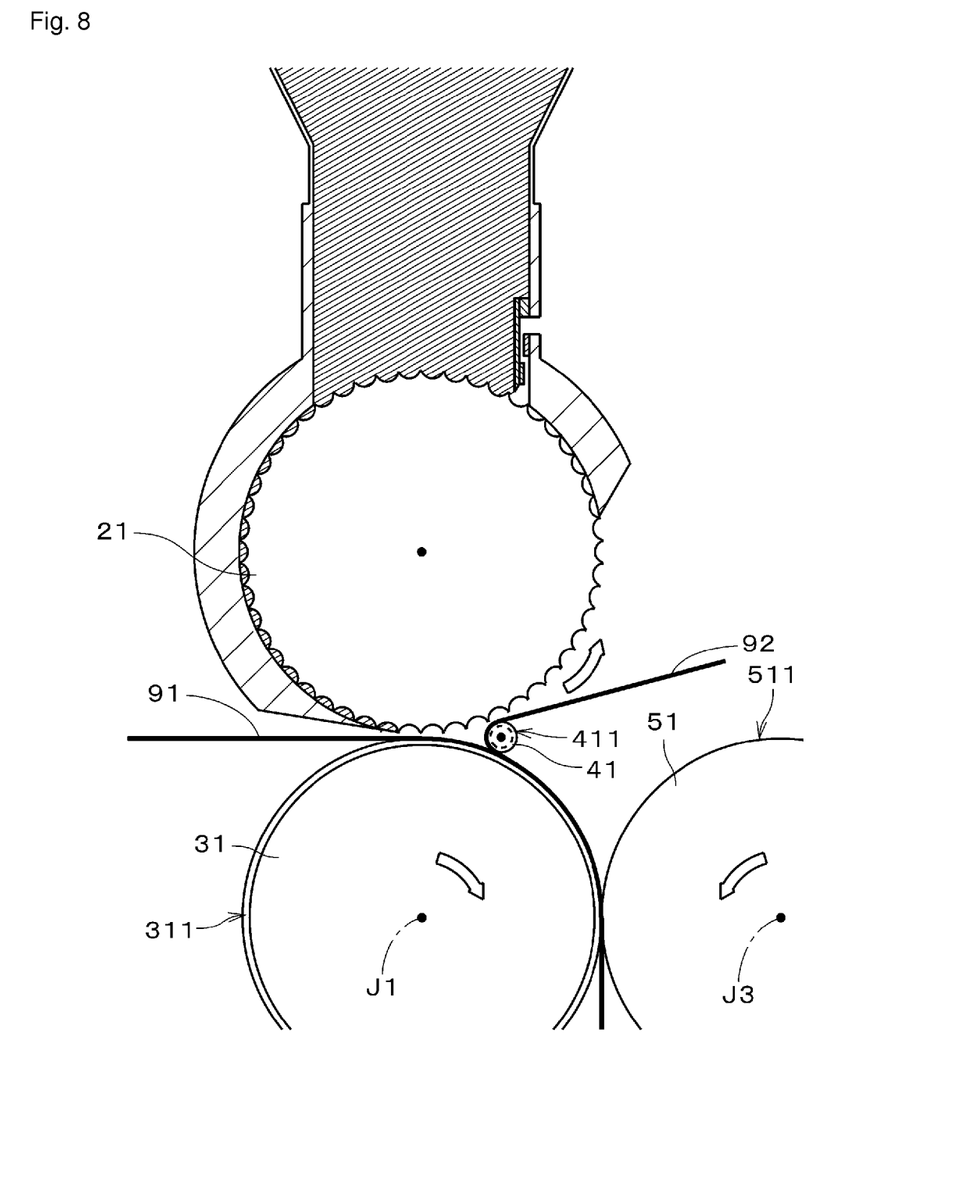
FIG. 8 is a view showing the vicinity of the cylinder part.

As mentioned previously, the positions of the annular grooves 412 in the second sheet conveying roller 41 are same as the positions of the concave portion rows 213 and the positions of the annular grooves 312 with respect to the axial direction, and the particles heading to the second sheet conveying roller 41 collide with portions of the second sheet member 92 lying right above the annular grooves 412 (i.e., portions at which the back surface is not in contact with any substance). As a result, the impact is absorbed and the particles are collected in the groove portions 911 of the first sheet member 91. As shown in FIG. 8, the second sheet member 92 is conveyed along the outer side surface 411 of the second sheet conveying roller 41, and (a portion of) the second sheet member 92 is placed (stacked) on (a portion of) the first sheet member 91 which has passed under the lowermost portion of the cylinder part 21.

Figure 9:
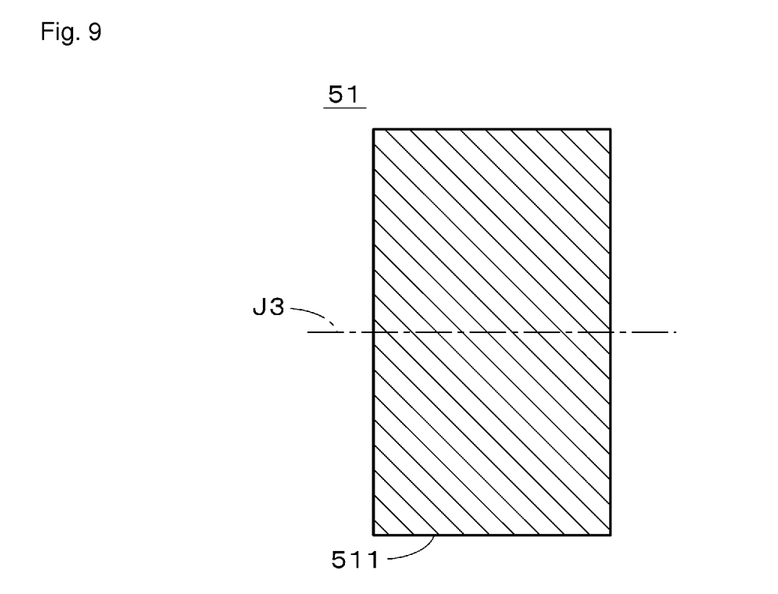
FIG. 9 is a cross-sectional view of a bonding roller.

FIG. 9 is a cross-sectional view of the bonding roller 51 and shows a cross section of the bonding roller 51 taken along a plane including the third central axis J3 of the bonding roller 51 in FIG. 1. The bonding roller 51 has an outer side surface 511 which is a cylindrical surface around the third central axis J3, and the outer side surface 511 is a smooth surface. As shown in FIG. 8, the first sheet member 91 supplied with particles and the second sheet member 92 overlaid on the first sheet member 91 are placed (sandwiched) between the outer side surface 311 of the first sheet conveying roller 31 and the outer side surface 511 of the bonding roller 51. The both (or one) of the first sheet conveying roller 31 and the bonding roller 51 are provided with heaters, and regions of the first sheet member 91 and the second sheet member 92 which come into contact with convex portions lying at both sides of each annular groove 312 (see FIG. 6) on the outer side surface 311 of the first sheet conveying roller 31 are heat-sealed, so that the first sheet member 91 and the second sheet member 92 are bonded with each other.

Figure 10:
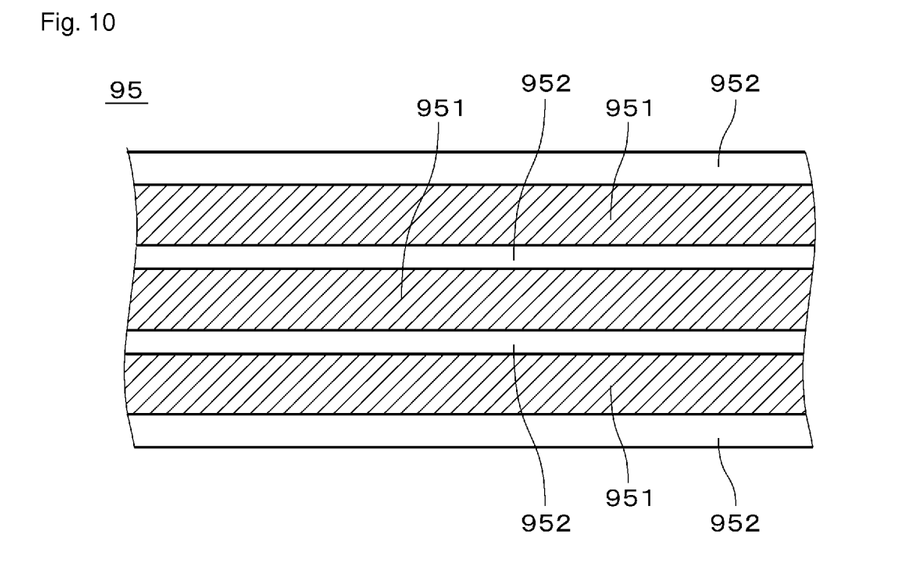
FIG. 10 is a plain view of an absorbent sheet.

Therefore, as shown in FIG. 10, an absorbent sheet 95 where a plurality of particle existence regions 951 and a plurality of particle non-existence regions 952 are alternately arranged in the width direction is formed. The plurality of particle existence regions 951 are strip-like (or linear) regions on each of which particles of high-absorbent resin are applied, and the plurality of particle non-existence regions 952 are strip-like (or linear) regions where particles don't exist essentially and the first sheet member 91 and the second sheet member 92 are bonded with each other. In other words, the plurality of particle existence regions 951 are provided in a stripe pattern in the absorbent sheet 95. In FIG. 10, hatching lines are drawn in the particle existence regions 951.

As described above, in the absorbent sheet manufacturing apparatus 1, the communication part 26 is located adjacent and posterior to the particle filling opening 232 in the rotation direction, and the concave portion 212a out of the plurality of concave portions 212 which faces the posterior edge of the particle filling opening 232 (i.e., faces the particle filling opening 232 at the posterior edge thereof) is in communication with the external space through the communication part 26. Therefore, when particles are filled into the concave portion 212a from the particle filling part 23, air in the concave portion 212a is forced out by particles entering the concave portion 212a and is easily discharged to the external space through the communication part 26. As a result, it is possible to increase a density of particles filled in the concave portion 212a. In addition, by the suction part 264 suctioning gas in the communication part 26, air in the concave portion 212a is discharged more efficiently and therefore, the density of particles filled in the concave portion 212a can be increased further.

In the absorbent sheet manufacturing apparatus 1, the particle filling opening 232 of the particle filling part 23 faces a portion including the uppermost portion of the cylinder part 21, and an aperture of the concave portion 212 becomes almost orthogonal to the vertical direction (i.e., gravity direction) in the vicinity of the uppermost portion of the cylinder part 21. Therefore, filling of particles into the concave portion 212 due to gravity is promoted and the density of particles filled in each concave portion 212 can be further increased. Since the particle tank 231 extends in almost parallel with the vertical direction, the self-weight of particles in the particle tank 231 exerting influence on particles in the concave portion 212 is almost constant from the posterior edge of the particle filling opening 232 to the anterior edge (i.e., across the entire length in the circumferential direction around the rotation axis R1). As a result, filling of particles into the concave portion 212 can be performed stably.

As discussed previously, in the communication part 26, the first end portion 261 facing the cylinder part 21 is positioned below the second end portion 262 facing the external space. This can reduce escape of particles from the concave portion 212a to the external space through the communication part 26. In addition, since the first end portion 261 is positioned almost right below the second end portion 262 in the vertical direction, escape of particles to the external space through the communication part 26 is further reduced. Furthermore, since the communication path 260 in the communication part 26 has many bending portions, escape of particles to the external space through the communication part 26 can be further reduced. The communication path 260 may bend at various positions toward various directions. From the viewpoint of reduction of escape of particles to the external space, it is preferable that the communication path 260 has at least two bending portions (i.e., the communication path 260 bends at least two points).

Though the preferred embodiments of the present invention have been discussed above, the present invention is not limited to the above-discussed preferred embodiments, but allows various variations.

For example, in the above preferred embodiment, the communication part 26 is provided across almost the entire extent where the three concave portion rows 213 are arranged in the axial direction of the cylinder part 21, however, three communication parts 26 corresponding to the three concave portion rows 213 may be provided independently of each other. In this case, there may be the case where the three communication parts 26 are connected to the suction part 264 individually, or second end portions 262 of the three communication parts 26 are connected to a common pipe and suction by the suction part 264 is performed through the common pipe. If particles are filled in the concave portion 212 at a sufficiently high density, suction by the suction part 264 may be omitted.

The first end portion 261 of the communication part 26 is not necessarily positioned right below the second end portion 262 in the vertical direction. If escape of particles to the external space through the communication part 26 is prevented or sufficiently reduced, for example, the second end portion 262 may be positioned on the same level as the first end portion 261 or below the first end portion 261.

If particles are filled in the concave portion 212 at a sufficiently high density, the particle filling opening 232 doesn't necessarily face a portion including the uppermost portion of the cylinder part 21 and may be located so as to face a portion anterior or posterior to the uppermost portion in the rotation direction of the cylinder part 21.

In the above preferred embodiment, discussion has been made on the manufacture (production) of the absorbent sheets 95 where the striped particle existence regions 951 are set, however, absorbent sheets having point-like (dotted) particle existence regions may be formed by decreasing the rotation speed of the cylinder part 21 or increasing spaces between adjacent concave portions 212 in the circumferential direction in the cylinder part 21.

The above cylinder part 21, first sheet conveying roller 31, first cover part 221, second cover part 222, particle filling part 23 and communication part 26 which function as a particle supplying apparatus for supplying particles of high-absorbent resin onto a sheet member may be utilized (combined) in various apparatuses other than the absorbent sheet manufacturing apparatus. For example, there may be a case where a sheet member whose upper surface is supplied with pulp fibers or the like is conveyed by the first sheet conveying roller 31 and particles of high-absorbent resin are supplied onto the pulp fibers by the cylinder part 21. In this case, particles filled in each concave portion 212 at a high density can be mixed with the pulp fibers.

In the above particle supplying apparatus, particles of absorbent material are supplied such as crosslinked partially neutralized polyacrylic acid, hydrolyzed starch-acrylic acid graft polymer, saponified vinyl acetate-acrylic ester copolymer, hydrolyzed acrylonitrile copolymer, crosslinked acrylonitrile copolymer, hydrolyzed acrylamide copolymer, crosslinked acrylamide copolymer, crosslinked cationic monomers, or crosslinked polyamino acid. The particle supplying apparatus may be utilized as an apparatus for supplying particles of deodorant material such as activated carbon, silica, alumina, zeolite, ion-exchange resin, or molecular sieve onto a sheet member. In this case, a sheet article manufacturing apparatus having the above particle supplying apparatus manufactures a deodorant sheet which is a sheet article for an absorbent article such as a disposable diaper or absorbent pad for light incontinence.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 Absorbent sheet manufacturing apparatus
21 Cylinder part
23 Particle filling part
26 Communication part
31 First sheet conveying roller
41 Second sheet conveying roller
51 Bonding roller
91 First sheet member
92 Second sheet member
95 Absorbent sheet
211 Outer side surface
212, 212a Concave portion
221 First cover part
222 Second cover part
232 Particle filling opening
260 Communication path
261 First end portion
262 Second end portion
264 Suction part
R1 Rotation axis

The invention claimed is:

1. A particle supplying apparatus for supplying particles of absorbent material or deodorant material onto a sheet member, comprising:
a cylinder part which has an generally cylindrical shape rotated around a rotation axis along a horizontal direction, said cylinder part having a plurality of concave portions arranged in a circumferential direction on an outer side surface thereof;
a particle filling part which is located above said cylinder part and which stores particles of absorbent material or deodorant material, to sequentially fill said plurality of concave portions with particles by a particle filling opening which faces said outer side surface of said cylinder part;
a first cover part which spreads from said particle filling opening along a rotation direction of said cylinder part to cover a portion of said outer side surface of said cylinder part;
a second cover part which spreads from said particle filling opening along an opposite direction of said rotation direction to cover another portion of said outer side surface of said cylinder part;
a communication part which is located adjacent and posterior to said particle filling opening in said rotation direction, a concave portion out of said plurality of concave portions being in communication with external space through said communication part, said concave portion facing a posterior edge of said particle filling opening; and
a sheet conveying part for conveying a sheet member in a direction under an anterior edge of said first cover part in said rotation direction, said direction being same as a moving direction of said outer side surface of said cylinder part.

2. The particle supplying apparatus according to claim 1, wherein said particle filling opening faces a portion including an uppermost portion of said cylinder part.

3. The particle supplying apparatus according to claim 2, further comprising a suction part for suctioning gas in said communication part.

4. A sheet article manufacturing apparatus for manufacturing a sheet article for an absorbent article, comprising:
a particle supplying apparatus according to claim 3;
another sheet conveying part for conveying another sheet member; and
a sheet bonding part for placing said another sheet member on said sheet member which has been supplied with particles by said particle supplying apparatus, to bond said another sheet member on said sheet member.

5. The particle supplying apparatus according to claim 1, wherein one end portion of said communication part which faces said cylinder part is positioned below the other end portion of said communication part.

6. A sheet article manufacturing apparatus for manufacturing a sheet article for an absorbent article, comprising:
a particle supplying apparatus according to claim 5;
another sheet conveying part for conveying another sheet member; and
a sheet bonding part for placing said another sheet member on said sheet member which has been supplied with particles by said particle supplying apparatus, to bond said another sheet member on said sheet member.

7. The particle supplying apparatus according to claim 5, further comprising a suction part for suctioning gas in said communication part.

8. A sheet article manufacturing apparatus for manufacturing a sheet article for an absorbent article, comprising:
a particle supplying apparatus according to claim 7;
another sheet conveying part for conveying another sheet member; and
a sheet bonding part for placing said another sheet member on said sheet member which has been supplied with particles by said particle supplying apparatus, to bond said another sheet member on said sheet member.

9. The particle supplying apparatus according to claim 1, wherein a communication path in said communication part has at least two bending portions.

10. A sheet article manufacturing apparatus for manufacturing a sheet article for an absorbent article, comprising:
a particle supplying apparatus according to claim 9;
another sheet conveying part for conveying another sheet member; and
a sheet bonding part for placing said another sheet member on said sheet member which has been supplied with particles by said particle supplying apparatus, to bond said another sheet member on said sheet member.

11. The particle supplying apparatus according to claim 9, further comprising a suction part for suctioning gas in said communication part.

12. A sheet article manufacturing apparatus for manufacturing a sheet article for an absorbent article, comprising:
a particle supplying apparatus according to claim 11;
another sheet conveying part for conveying another sheet member; and
a sheet bonding part for placing said another sheet member on said sheet member which has been supplied with particles by said particle supplying apparatus, to bond said another sheet member on said sheet member.

13. The particle supplying apparatus according to claim 1, further comprising a suction part for suctioning gas in said communication part.

14. A sheet article manufacturing apparatus for manufacturing a sheet article for an absorbent article, comprising:
- a particle supplying apparatus according to claim 13;
- another sheet conveying part for conveying another sheet member; and
- a sheet bonding part for placing said another sheet member on said sheet member which has been supplied with particles by said particle supplying apparatus, to bond said another sheet member on said sheet member.

15. A sheet article manufacturing apparatus for manufacturing a sheet article for an absorbent article, comprising:
- a particle supplying apparatus according to claim 1;
- another sheet conveying part for conveying another sheet member; and
- a sheet bonding part for placing said another sheet member on said sheet member which has been supplied with particles by said particle supplying apparatus, to bond said another sheet member on said sheet member.

16. A sheet article manufacturing apparatus for manufacturing a sheet article for an absorbent article, comprising:
- a particle supplying apparatus according to claim 2;
- another sheet conveying part for conveying another sheet member; and
- a sheet bonding part for placing said another sheet member on said sheet member which has been supplied with particles by said particle supplying apparatus, to bond said another sheet member on said sheet member.

* * * * *